United States Patent [19]

Knute et al.

[11] Patent Number: 5,107,847
[45] Date of Patent: Apr. 28, 1992

[54] FIBER-OPTIC TRANSDUCER APPARATUS

[75] Inventors: Wallace L. Knute, Del Mar; Wilber H. Bailey, Leucadia, both of Calif.

[73] Assignee: Camino Laboratories, San Diego, Calif.

[21] Appl. No.: 535,974

[22] Filed: Jun. 8, 1990

Related U.S. Application Data

[63] Continuation of Ser. No. 456,221, Dec. 20, 1989, abandoned, which is a continuation of Ser. No. 344,551, Apr. 25, 1989, abandoned, which is a continuation of Ser. No. 253,876, Oct. 5, 1988, abandoned, which is a continuation of Ser. No. 165,345, Feb. 29, 1988, abandoned, which is a continuation of Ser. No. 56,274, May 26, 1987, abandoned, which is a continuation of Ser. No. 904,799, Sep. 3, 1986, abandoned, which is a continuation of Ser. No. 777,854, Sep. 18, 1985, abandoned, which is a continuation of Ser. No. 498,092, May 25, 1983, abandoned.

[51] Int. Cl.$^5$ ............................................. A61B 5/00
[52] U.S. Cl. .................................... 128/675; 128/667; 73/705
[58] Field of Search .................... 128/665-667, 128/675, 748; 250/230, 232, 578.1; 73/703, 705, 715, 727

[56] References Cited

U.S. PATENT DOCUMENTS

| | | | |
|---|---|---|---|
| 2,441,882 | 5/1948 | Hicks | 73/729 |
| 3,051,003 | 8/1962 | Witt | 73/705 |
| 3,068,739 | 12/1962 | Hicks, Jr. et al. | |
| 3,249,105 | 5/1966 | Polanyi | 128/675 |
| 3,267,932 | 8/1966 | Valliere | 128/675 |
| 4,201,222 | 5/1980 | Haase | 128/667 |
| 4,210,029 | 7/1980 | Porter | 73/705 |
| 4,249,076 | 2/1981 | Bergstrom et al. | 250/227 |
| 4,260,883 | 4/1981 | Onoda et al. | 250/226 |
| 4,358,960 | 11/1982 | Porter | 73/705 |
| 4,487,206 | 12/1984 | Aagard | 128/667 |

FOREIGN PATENT DOCUMENTS 2849186 6/1979 Fed. Rep. of Germany.

Primary Examiner—Kyle L. Howell
Assistant Examiner—John P. Lacyk
Attorney, Agent, or Firm—Fulwider Patton Lee & Utecht

[57] ABSTRACT

A fiber-optic transducer apparatus, and a related method of manufacturing it, for particular use in medical applications such as invasive blood pressure and body temperature measurement. The apparatus includes a catheter comprised of a sheath and an enclosed first set of optical fibers for transmitting a light beam to and from the remote end of the catheter, where a transducer modulates it in accordance with the variable to be measured, e.g., blood pressure. A photosensor located at the near end of the catheter measures the modulated intensity of the returned beam, to produce a corresponding measurement signal. The catheter is further comprised of a second set of optical fibers located within the sheath, for transmitting a reference light beam to and from the remote end of the catheter. A second photosensor measures the intensity of the returned reference light beam, to produce a correction signal indicative of variations in transmittance caused by bending of the catheter. It is presumed that the effects of such bending are the same for the second set of optical fibers as for the first set, so the apparatus adjusts the measurement signal in accordance with the correction signal, to produce an adjusted measurement signal that is substantially insensitive to the effects of such bending.

18 Claims, 2 Drawing Sheets

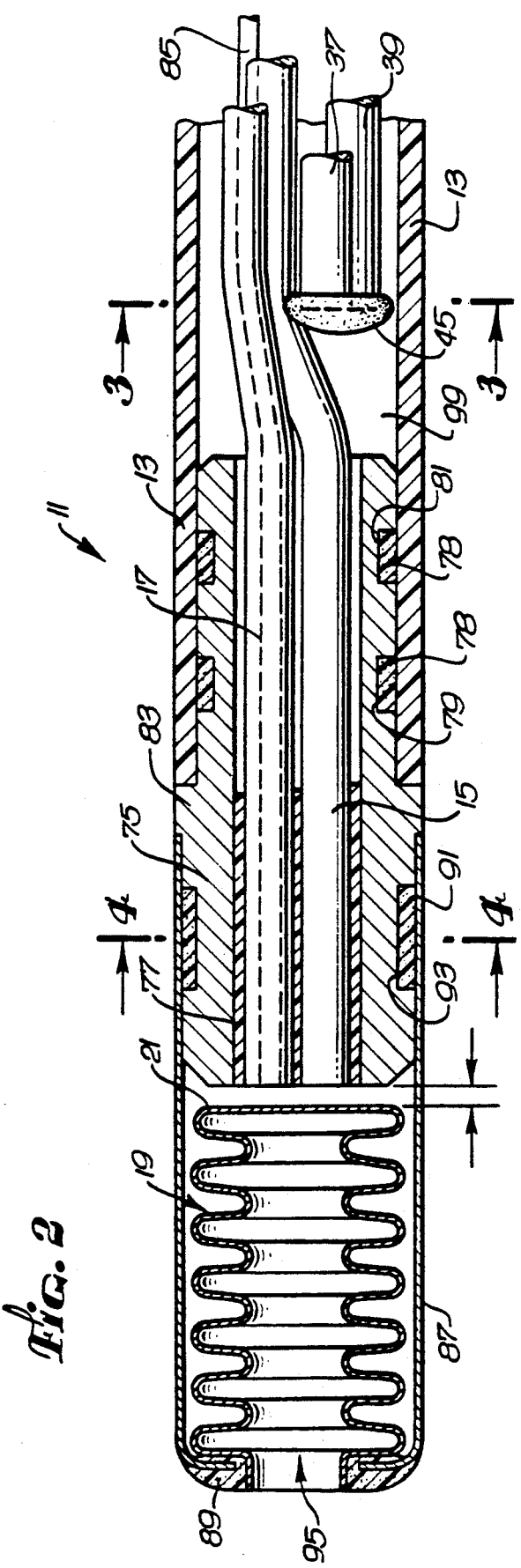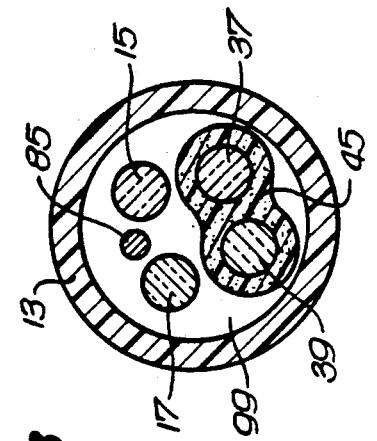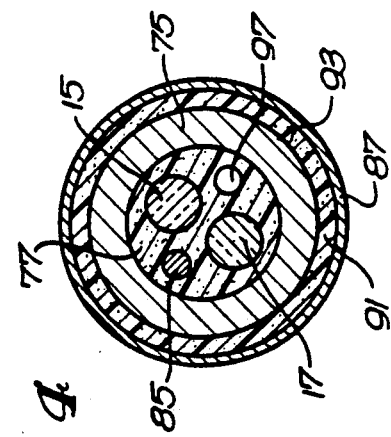

FIBER-OPTIC TRANSDUCER APPARATUS

BACKGROUND OF THE INVENTION

This invention relates generally to transducer systems for measuring physical variables and, more particularly, to systems of this kind that transmit a modulated light beam along an optical fiber.

Optical transducer systems of this particular kind have been used in the past in the medical field for such applications as measuring a patient's blood pressure, intra-cranial pressure, body temperature, etc. The typical system includes a catheter comprised of two sets of optical fibers located within a resilient sheath, which is adapted for insertion into a patient's body. One set of fibers transmits a light beam to a transducer located at the remote end of the catheter, and the other set of fibers returns a modulated light beam from the transducer. The transducer modulates the beam by reflecting to the second set of fibers a proportion of the light beam that varies in accordance with the variable being measured. A photosensor senses the intensity of the returned light beam, to produce a signal indicative of the variable.

Fiber-optic transducer systems such as the one described above have not proven to be entirely satisfactory, and have not as yet met with widespread acceptance. One reason for this apparent lack of acceptability is believed to be that bending of the catheter can affect the intensity of the light beam returned from the transducer. The user cannot be sure whether a particular drop in signal level is due to an actual change in the variable being measured or to bending of the catheter. In addition, movement of the catheter can modulate the intensity of the returned light beam and thereby make it difficult to measure the variable accurately.

It should therefore be appreciated that there is a definite need for a fiber-optic transducer apparatus that is not susceptible to output signal variations caused by bending or movement of the fibers. The present invention fulfills these needs.

SUMMARY OF THE INVENTION

The present invention is embodied in an optical transducer apparatus for use in measuring a predetermined physical variable and producing a corresponding measurement signal. The apparatus includes optical fiber means for transmitting a light beam to and from a remote location, along with transducer means located at the remote location for modulating the intensity of the beam in accordance with the magnitude of the variable to be measured. Photosensor means responsive to the modulated light beam returned by the optical fiber means produces a measurement signal indicative of its modulated intensity. An undesired characteristic of the optical fiber means is that bending of it can cause variations in its light transmittance. In accordance with the invention, the apparatus further includes correction means for adjusting the measurement signal to correct for variations in the transmittance of the optical fiber means, such that the corrected signal more accurately represents the variable being measured. This enables the apparatus to accurately measure the variable even though the optical fiber means might be bent by an unknown amount.

More particularly, the invention is embodied in a fiber-optic transducer apparatus that includes a catheter comprised of at least two optical fibers carried within a sheath. One fiber supplies a light beam to the transducer means located at its remote end, and the other fiber returns the beam after modulation by the transducer. This structure is particularly useful in medical applications, for insertion into a patient's vascular system or into the space between the patient's skull and cerebrum, to measure variables such as blood pressure, body temperature or intra-cranial pressure. In the case of a blood pressure transducer, the transducer can conveniently include a light-reflective diaphragm such as a bellows that is movable in accordance with pressure, to vary correspondingly the proportion of light reflected from the first fiber to the second fiber.

In applications such as these, the sheath and optical fibers are necessarily bent to at least a limited extent, thereby invariably causing variations in the light transmittance of the fibers. Unfortunately, merely monitoring the intensity of the returned light beam does not tell the user whether or not a given change in intensity is due to a variation in pressure or a variation in bending.

The correction means includes second optical fiber means located within the same sheath as the first optical fiber means. The second optical fiber means includes at least one fiber for transmitting a light beam to the remote location and another fiber for returning light from the location, with reflector means located at the remote location for directing a predetermined proportion of the beam supplied by the first fiber to the second fiber. In addition, the correction means includes second photosensor means for measuring the intensity of the light beam returned by the second optical fiber means and for adjusting the measurement signal accordingly. The reflector means preferably includes a translucent epoxy material bonding together the remote ends of two fibers of the second optical fiber means.

The respective light beams transmitted by the first and second optical fiber means are produced by a single light source, and the correction means is preferably connected to the light source, to controllably adjust the intensities of the two beams so as to correct for variations in the light transmittance of the optical fiber means. In particular, the light source is regulated such that the second light beam returned by the second optical fiber means has a substantially constant intensity, regardless of the degree of bending of the respective optical fibers. Since the fibers of the first and second optical fiber means are all located within the same sheath, and thus experience substantially the same amount of bending, it is presumed that such bending has the same effect on the first optical fiber means as on the second optical fiber means. Regulating the intensity of the returned reference light beam to a prescribed fixed level therefore ensures that any such bending will have a minimal effect on the intensity of the returned first light beam.

In another aspect of the invention, the transducer means includes rigid termination means in the preferred form of a sleeve, along with attachment means such as an epoxy material for attaching the remote ends of the sheath and first optical fiber means to the sleeve. In addition, the catheter preferably further includes a wire located within the sheath and extending for its entire length. The wire is attached at its remote end by the attachment means and at its near end to a circuit board. In addition, the length of the wire is slightly less than that of the sheath and first optical fiber means, so that any tensile stress applied to the catheter is withstood primarily by the wire. This protects the fibers and sheath from damage. The fibers of the second optical fiber means preferably terminate just short of the sleeve.

Other aspects and advantages of the present invention should become apparent from the following description of the preferred embodiment, taken in conjunction with the accompanying drawings, which illustrate, by way of example, the principles of the invention.

BRIEF DESCRIPTION OF THE DRAWINGS

FIG. 2 is a cross-sectional view of the remote end of the, fiber-optic catheter of FIG. 1, showing the remote ends of the optical fibers and a pressure-responsive bellows;

FIG. 3 is a cross-sectional view of the catheter taken in the direction of the arrows 3—3 in FIG. 2;

FIG. 4 is a cross-sectional view of the catheter, taken in the direction of the arrows 4—4 in FIG. 2.

DESCRIPTION OF THE PREFERRED EMBODIMENT

Figure 1:
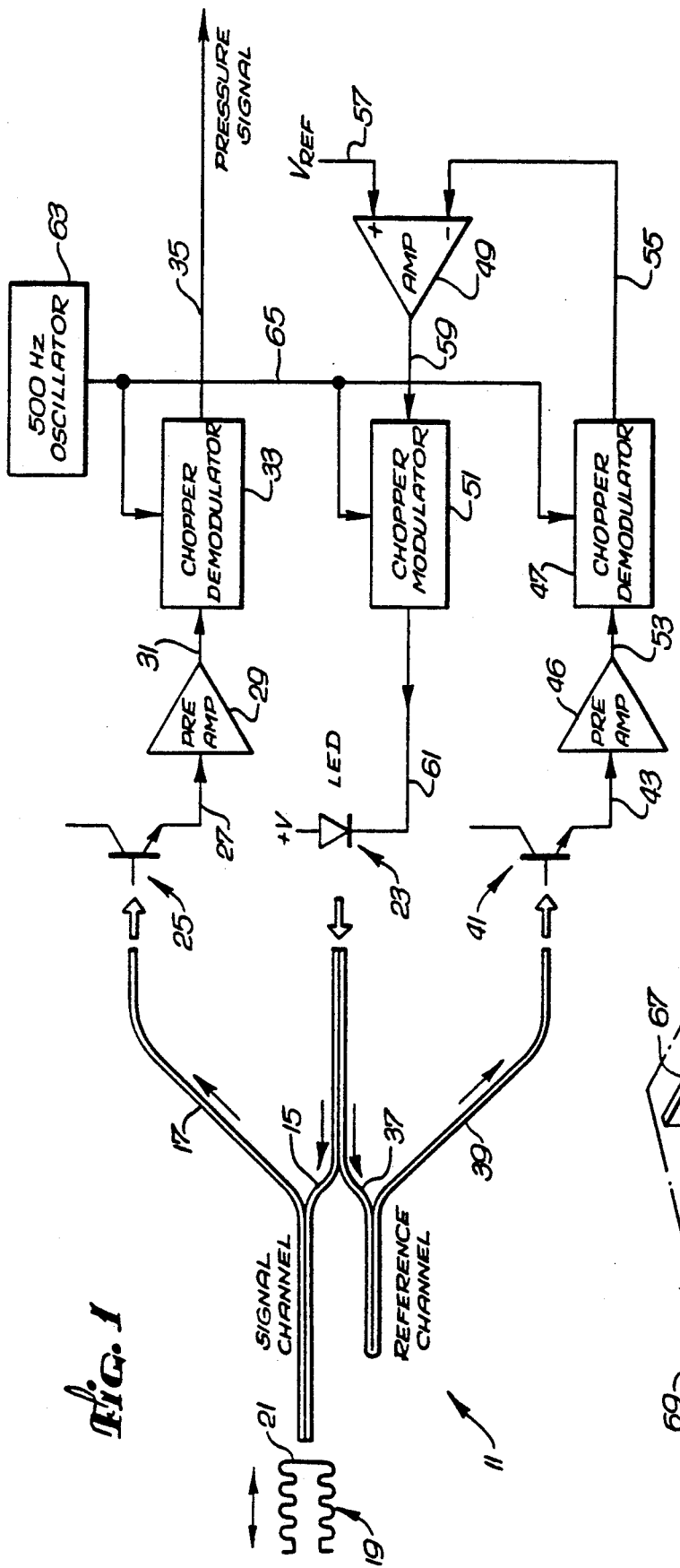
FIG. 1 is a simplified schematic diagram of a pressure transducer apparatus embodying the present invention.

Referring now to the drawings, and particularly to FIGS. 1 and 2, there is shown a fiber-optic pressure transducer adapted for insertion into a patient's vascular system to measure blood pressure. The apparatus includes a catheter 11 comprised of a polyurethane sheath 13 (FIG. 2) and a first set of optical fibers located within the sheath. The first set of fibers includes an emitter fiber 15 and a return fiber 17 for transmitting a first light beam to and from the catheter's remote end. A pressure transducer having a bellows 19 with a light-reflective surface 21 that moves in accordance with pressure is located at the catheter's remote end, for modulating the intensity of the first light beam.

A light-emitting diode (LED) 23 produces the light beam for transmission by the first set of optical fibers, and a first phototransistor 25 detects the modulated intensity of the returned beam. The phototransistor produces an intensity signal on line 27 having an electrical current that indicates the patient's blood pressure. This signal is amplified in a preamplifier 29 and coupled, in turn, on line 31 to a chopper demodulator 33, whose function is described below. The demodulator produces an analog pressure signal for output on line 35.

Since the catheter 11 is adapted for insertion into the patient's vein or artery, it necessarily experiences at least limited bending. This unfortunately affects the light transmittance of both the emitter fiber 15 and the return fiber 17, and therefore correspondingly affects the magnitude of the intensity signal produced by the first phototransistor 25. The light transmittance of the fibers can also vary with temperature. In addition, the efficiency of the LED 23 can vary with temperature and aging, and the efficiency of the phototransistor can vary with temperature. These variations result in corresponding changes in the intensity signal.

In accordance with the invention, the transducer apparatus further includes a reference channel comprised of a second set of optical fibers, located within the sheath 13 and extending substantially along its entire length. This reference channel is used to determine the effects of bending on transmittance and to determine the effects of temperature and aging on the efficiencies of the LED 23 and phototransistor 25. Since the first and second sets of optical fibers are substantially co-extensive and experience substantially the same degree of bending, the effect of that bending on their respective transmittances is presumed to be substantially equivalent. A second light beam produced by the LED 23 is transmitted by the second set optical fibers so that variations in the fibers' transmittance and variations in the LED's efficiency can be determined and a corresponding correction made to the intensity signal.

The second set of optical fibers includes an emitter fiber 37 for transmitting the second light beam from the LED 23 to a location near the end of the catheter 11 and a return fiber 39 for transmitting the light beam back from that location. A second phototransistor 41 detects the intensity of this returned light beam, to produce a correction signal on line 43 having an electrical current whose magnitude is proportional to intensity. The two phototransistors 25 and 41 are normally maintained at the same temperature, so their respective efficiencies tend to track each other.

A translucent droplet 45 of an epoxy containing a white pigment bonds together the remote ends of the two fibers and thereby reflects a predetermined fixed proportion of the light beam from the emitter fiber to the return fiber. The epoxy droplet is preferably coated with an opaque silver paint, the opacity preventing movement of adjacent elements from affecting the return beam and the silver color maximizing the intensity of the return beam.

In the preferred embodiment, the second set of optical fibers is part of a feedback control system for regulating the current applied to the LED 23 so as to compensate for the variable light transmittance of the fibers and for the variable efficiencies of the LED 23 and phototransistors 25 and 41. Thus, if the transmittance of the second set of fibers decreases or if the efficiency of the LED decreases, for example, the control system automatically increases the drive current applied to the LED so that the intensity of the returned beam detected by the second phototransistor 41 remains substantially constant.

Besides the second set of optical fibers, the feedback control system includes the LED 23, the second phototransistor 41, a preamplifier 46, a chopper demodulator 47, a differential amplifier 49, and a chopper modulator 51. The correction signal produced by the second phototransistor is coupled on line 43 to the preamplifier for amplification, and coupling, in turn, on line 53 to the chopper demodulator, whose function is described below. The chopper demodulator outputs a signal proportional to the intensity of the returned second light beam for coupling on line 55 to the negative input terminal of the differential amplifier. A prescribed reference voltage is connected on line 57 to the amplifier's positive input terminal. The resulting error signal is transmitted on line 59 from the differential amplifier to the chopper modulator, whose function is described below, and in turn over line 61 to the LED.

The apparatus further includes chopper circuitry for preventing any dc offsets in the various circuit elements from affecting the pressure measurement being made. This chopper circuitry includes the previously-mentioned chopper demodulators 33 and 47 and chopper modulator 51, and in addition includes a 500 Hz oscillator 63, which produces a 500 Hz clock signal for coupling on line 65 to each demodulator and to the modulator. The modulator is essentially an analog gate for turning on and off the LED 23 at the 500 Hz rate, so that the electrical current signals produced by the first and second phototransistors 25 and 41, respectively, are modulated correspondingly. The two chopper demodulators are essentially sample-and-hold circuits for gating through the corresponding voltage signals only during those times when the LED is energized. As previously mentioned, this chopper circuitry ensures that any dc offsets in the various circuit elements do not affect the accuracy of the pressure measurement being made.

A perspective view of the coupling of the first and second sets of optical fibers to the LED 23 and phototransistors 25 and 41, respectively, is provided in FIG. 3. The electrical circuitry depicted schematically in FIG. 1 is mounted on a circuit board 67 located within a housing 69 and having a plurality of terminal pins 71 adapted for connection to additional processing circuitry (not shown). The various fibers of the first and second sets of optical fibers are optically coupled to the LED and phototransistors by means of a transparent optical gel potting material. In particular, each optical fiber is positioned with its end abutting the light-emitting surface of the LED or light-sensitive surface of the phototransistors. The potting material is deposited around the ends of the fibers, and a portion of it flows into any space located between the fibers and the surfaces. This provides an efficient coupling of light between the surfaces and their respective fibers.

Figure 5:
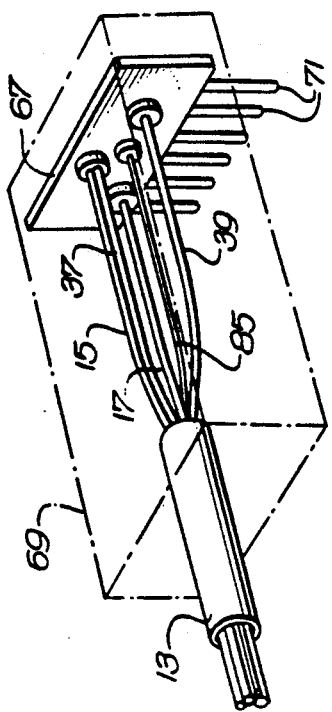
FIG. 5 is a perspective view of a portion of the transducer apparatus, depicting the near end of the fiber-optic catheter and the connections between its optical fibers and the light-emitting diode and photo-transistors.

The bellows 19 and the remote ends of the sheath 13 and the first and second sets of optical fibers are depicted in detail in FIGS. 2, 4 and 5. The remote ends of the emitter fiber 15 and return fiber 17 of the first set are epoxied inside a stainless steel sleeve 75 that is coaxial with the sheath. The sleeve's inside diameter is slightly greater than the combined diameters of the two fibers (see FIG. 4), so that they readily fit within it. The epoxy, which is designated by the numeral 77, is drawn into the space between the fibers and the sleeve's inside wall for a distance of about one-half the sleeve's length. The remote ends of the two fibers are ground and polished flush with the far end of the sleeve, to provide an efficient optical coupling between the fibers and the light-reflective surface 21 of the bellows 19. This surface extends beyond the periphery of the sleeve opening, as shown in FIG. 2, to accommodate all possible locations for the remote ends of the two fibers within the sleeve.

The remote end of the sheath 13 is epoxied to the outside surface of the sleeve 75. In particular, a mass of epoxy designated by the numeral 78 is located within a pair of channels 79 and 81 encircling the sleeve's outside surface. An annular flange 83 serves as a convenient stop for the sheath's remote end. The outside diameter of the flange is substantially equal to that of the sheath, i.e., about 0.049 inches, so as not to present any diameter discontinuity that might interfere with insertion of the catheter 11 into the patient's vein or artery.

The sheath 13 and the two fibers 15 and 17 of the first set of optical fibers have limited tensile strength and cannot, by themselves, withstand a substantial tensile stress. To alleviate this problem, the catheter 11 further includes a 0.006 inch diameter wire 85 located within the sheath and connected between the circuit board 67 and the sleeve 75. It is attached to the inside wall of the sleeve by the epoxy material 77. The portion of the wire encased by the epoxy can have a slight bend or crimp in it to provide a stronger grip. The wire is preferably about one-eighth inch shorter than the first set of optical fibers, so that the wire, and not the fibers, withstands any applied tensile stress. The additional fiber length is accounted for simply by a small amount of coiling within the sheath.

The remote ends of the emitter fiber 37 and return fiber 39 of the second set of optical fibers terminate just short of the near end of the sleeve 75, so as to be coextensive with the first set of fibers for as long a distance as is practical. As previously mentioned, the fibers are bonded together by a translucent droplet 45 of epoxy, which reflects a predetermined proportion of the second light beam from the emitter fiber to the return fiber.

The pressure-sensitive bellows 19 is positioned a prescribed distance away from the remote ends of the first set of optical fibers by means of a stainless steel cover 87. In particular, the bellows is disposed within an opening in one end of the cover and secured in place by means of an epoxy material, designated by the numeral 89. The cover, in turn, is secured to the outside surface of the sleeve 75 by means of an epoxy material, designated by the numeral 91, located within channel 93 encircling the sleeve's outside surface. The annular flange 83 serves as a convenient stop for positioning the cover relative to the fibers 15 and 17 secured within the sleeve. The cover and flange have equal outside diameters.

The top surface 21 of the pressure-sensitive bellows 19, which confronts the remote ends of the emitter fiber 15 and return fiber 17 of the first set of optical fibers, is preferably plated with gold, to enhance reflectivity of the first light beam. This gold plating is preferably performed after the bellows has been epoxied to the cover 87, using an electroless process.

In the preferred embodiment, the emitter and return fibers 15 and 17 of the first set of optical fibers both have a diameter of 0.010 inches, and the light-reflective surface 21 of the bellows 19 is positioned about 0.003 inches from their remote ends. At this spacing, relative axial movement of the bellows provides a high rate of change of optical coupling between the two fibers.

Several factors inherent in the manufacturing of the catheter 11 cause an uncertainty or inaccuracy in the relationship between the patient's actual blood pressure and the magnitude of the output pressure signal. These factors include uncertainties in the sensitivity of the bellows 19 and uncertainties in the relative positions of the remote ends of the two fibers 15 and 17 within the sleeve 75. Any such inaccuracy associated with the output pressure signal can be compensated for by appropriately calibrating each catheter. In particular, this can be accomplished by including special code circuitry (not shown) on the circuit board 67 associated with each catheter. An example of such code circuitry and of a system for utilizing it to provide a calibrated measurement signal is described in U.S. Pat. No. 4,446,715 entitled "Transducer Calibration System."

In use, the catheter 11 is positioned in a patient's vein or artery and blood enters the hollow core 95 of the bellows 19, to press against the underside of its top wall. The opposite side of the top wall, i.e., the light-reflective surface 21 is vented to atmospheric pressure through a port 97 formed in the epoxy 77 located within the sleeve 75 and, in turn, through the empty space 99 within the sheath 13. The port 97 is formed by placing a wire through the sleeve when the epoxy if first inserted, and by removing the wire after the epoxy has hardened and the ends of the fibers 15 and 17 have been ground and polished.

It should be appreciated from the foregoing description that the present invention provides an improved transducer apparatus having a fiber-optic catheter for particular use in medical applications such as invasive blood pressure and body temperature measurement. The apparatus includes a first set of optical fibers located within a sheath and transmitting a light beam to and from a remote transducer, which modulates the beam in accordance with the variable to be measured. A second set of optical fibers, which is likewise located within the sheath and is substantially co-extensive with the first set, is used to detect any variation in the light transmittance of the fibers caused by factors such as bending. The apparatus then controllably adjusts its measurement of the variable so as to correct for the effects of such varying transmittance.

Although the invention has been described in detail with reference to the presently-preferred embodiment, it should be understood by those of ordinary skill in the art that various modifications can be made without departing from the invention. Accordingly, the invention is limited only by the following claims.

I claim:

1. In a measurement system having a transducer for measuring a predetermined variable, an optical processing apparatus comprising:
   a light source positioned at a location remote from the transducer;
   a transducer coupling means for modulating a light beam in accordance with the predetermined variable measured by the transducer;
   first optical fiber means for receiving light from the light source, forming said received light into a light beam, transmitting said light beam to said transducer coupling means, receiving the modulated light beam from said transducer coupling means, and conducting said received, modulated light;
   first photosensor means for receiving said modulated light conducted by the first optical fiber means and for producing a measurement signal indicative of the modulation of the light received from the first optical fiber means;
   a reflector fixed in a position near, but separate from the transducer coupling means;
   a reference-emitter optical fiber means for receiving light from the light source, and transmitting from its remote end the received light to said reflector;
   a reference-return optical fiber means for receiving at its remote end light reflected by the reflector and conducting said received light;
   wherein the reference-emitter and reference-return fiber means are substantially coextensive with the first optical fiber means;
   second photosensor means for receiving said light conducted by the reference-return optical fiber means and for producing a correction signal indicative of the intensity of the light received from the reference-return optical fiber means; and
   correction means for receiving the correction signal and adjusting the measurement signal in response thereto;
   wherein said reflector encloses the remote ends of the reference-emitter and the reference-return optical fiber means.

2. Optical processing apparatus as defined in claim 1, wherein:
   the first optical fiber means includes an emitter fiber means for directing the light beam at the transducer coupling means and a return fiber means for receiving light modulated by the transducer coupling means.

3. Optical processing apparatus as defined in claim 1, wherein:
   the first optical fiber means includes:
   an emitter fiber means having proximal and remote ends, for receiving at its proximal end light from the light source, forming said received light into the light beam and transmitting from its source end the light beam to the transducer coupling means;
   a return fiber means having proximal and remote ends, for receiving at its remote end the light beam modulated by the transducer coupling means and conducting said received modulated light to the first photosensor means; and
   the apparatus further includes a sheath surrounding the emitter, return, reference-emitter and reference-return fiber means.

4. Optical processing apparatus as defined in claim 3, further comprising:
   a rigid termination sleeve,
   attachment means for attaching the remote ends of the emitter fiber means, return fiber means and sheath to the rigid termination sleeve; and
   a wire means located within the sheath and attached by the attachment means to the rigid termination sleeve, the wire means for reducing tensile stress applied to the emitter fiber means, return fiber means and sheath.

5. Optical processing apparatus as defined in claim 4, wherein:
   the attachment means includes an epoxy material located within the sleeve which adheres to the sleeve and to the emitter and the return fiber means.

6. The optical processing apparatus of claim 1 wherein the reflector is disposed such that it is in contact with the remote ends of both the reference-emitter and the reference-return fiber means.

7. The optical processing apparatus of claim 6 wherein the reflector comprises a first layer of reflective material disposed in contact with the remote ends of both the reference-emitter and reference-return fiber means and a second layer of material which is substantially opaque.

8. The optical processing apparatus of claim 1 wherein the transducer coupling means comprises a reflecting surface for modulating the light beam.

9. In a measurement system having a transducer for measuring a predetermined variable, an optical processing apparatus comprising:
   a light source positioned at a location remote from the transducer;
   a transducer coupling means for modulating a light beam in accordance with the predetermined variable measured by the transducer;
   a sheath;
   first optical fiber means located within the sheath and including an emitter fiber means having proximal and remote ends for receiving at its proximal end light from the light source, forming said received light into a light beam and transmitting from its remote end said light beam at said transducer coupling means, and a return fiber means having a remote end for receiving the modulated light beam from the transducer coupling means and conducting said received modulated light;

first photosensor means for sensing the modulation of the light received by the return fiber means of the first optical fiber means and for producing a corresponding measurement signal;

light directing means fixed in position near but separate from the transducer coupling means for redirecting received light;

second optical fiber means located within the sheath and including a reference-emitter fiber means having proximal and remote ends for receiving at its proximal end light from the light source, and transmitting from its remote end said received light to the light directing means, and a reference-return fiber means having a remote end for receiving at its remote end light directed by the light directing means and conducting said received, directed light;

wherein the reference-emitter and reference-return fiber means are substantially coextensive with the first optical fiber means;

second photosensor means for sensing the intensity of the light conducted by the reference-return fiber means of the second optical fiber means and for producing a corresponding correction signal therefrom; and correction means for adjusting the measurement signal in accordance with the correction signal thereby minimizing errors in the measurement signal caused by variations in the transmittance of the first optical fiber means;

wherein said light directing means encloses the remote ends of the reference-emitter and the reference-return optical fiber means.

10. Optical processing apparatus as defined in claim 9, further comprising:

a sleeve having an inside surface and an outside surface; and epoxy means for rigidly securing the remote ends of the emitter fiber and return fiber of the first optical fiber means to the inside surface of the sleeve and for rigidly securing the remote end of the sheath to the outside surface of the sleeve.

11. Optical processing apparatus as defined in claim 10, wherein:

the sleeve is located beyond the remote ends of the reference-emitter fiber means and reference-return fiber means of the second optical fiber means;

the light directing means includes translucent epoxy means for bonding together the remote ends of the reference-emitter fiber means and the reference-return fiber means of the second optical fiber means.

12. Optical processing apparatus as defined in claim 10, and further including a wire located within the sheath and rigidly secured to the inside surface of the sleeve by the epoxy means, the wire being shorter in length than both the sheath and the first optical fiber means such that any tensile stress applied to the apparatus is withstood primarily by the wire.

13. The optical processing apparatus of claim 9 wherein the reflector is disposed such that it is in contact with the remote ends of both the reference-emitter and the reference-return fiber means.

14. The optical processing apparatus of claim 13 wherein the light directing means comprises a first layer of reflective material disposed in contact with the remote ends of both the reference-emitter and reference-return fiber means and a second layer of material which is substantially opaque.

15. The optical processing apparatus of claim 9 wherein the transducer coupling means comprises a reflecting surface for modulating the light beam.

16. In a measurement system having a transducer for measuring a predetermined variable, a fiber-optic processing apparatus comprising:

an elongated, generally cylindrical sheath having a remote end;

a light source positioned at a located remote from the transducer;

a first reflector means coupled to the transducer for used in modulating a light beam in accordance with the predetermined variable measured by the transducer;

first optical fiber means located within the sheath and including an emitter fiber means having proximal and remote ends for receiving at its proximal end a light beam from the light source, conducting said received light beam to the first reflector, and transmitting from its remote end the light beam to said first reflector, and a return fiber means having a remote end, for receiving at its remote end and returning reflected, modulated light from the first reflector;

a sleeve having an inside surface and an outside surface;

epoxy means for rigidly securing the remote end of the sheath to the outside surface of the sleeve and for rigidly securing the remote ends of the emitter fiber means and return fiber means of the first optical fiber means to the inside surface of the sleeve, in confronting relationship with the first reflector;

first photosensor means for sensing the intensity of the light returned by the return fiber means of the first optical fiber means and for producing a corresponding measurement signal;

a second reflector;

second optical fiber means located within the sheath and including a reference emitter fiber means having proximal and remote ends, for receiving at its proximal end a second beam from the light source, conducting said second beam and transmitting from its remote end the second light beam to the second reflector, and a reference-return fiber means having a remote end, for returning light reflected from the second reflector;

wherein the second optical fiber means are substantially coextensive with the first optical fiber means;

wherein the second reflector contacts and encloses the remote ends of the reference-emitter and reference-return fiber means of the second optical fiber means for directing a predetermined proportion of the second light beam from the reference-emitter fiber means to the reference-return fiber means;

wherein the sleeve is located beyond the remote ends of the reference-emitter fiber means and reference-return fiber means of the second optical fiber means;

second photosensor means for sensing the intensity of the reflected light beam returned by the second optical fiber means and for producing a corresponding correction signal;

correction means connected to the light source for controllably adjusting the intensity of the first and second light beams it produces in accordance with the correction signal, such that the second light beam returned by the second optical fiber means has a substantially constant intensity, thereby minimizing errors in the measurement signal caused by variations in the transmittance of the first optical fiber means; and a wire located within the sheath and rigidly secured to the inside surface of the sleeve by the epoxy means, the wire being shorter in length than both the sheath and the first optical fiber means such that any tensile stress applied to the apparatus is withstood primarily by the wire.

17. The optical processing apparatus of claim 16 wherein the second reflector includes translucent epoxy means bonding together the remote ends of the reference-emitter fiber means and reference-return fiber means of the second optical fiber means.

18. The optical processing apparatus of claim 16 wherein the second reflector comprises a first layer of reflective material in contact with and facing towards the reference-return fiber means and a second layer of material which is substantially opaque.

* * * * *

UNITED STATES PATENT AND TRADEMARK OFFICE
CERTIFICATE OF CORRECTION

PATENT NO. : 5,107,847
DATED : April 28, 1992
INVENTOR(S) : Knute et al.

It is certified that error appears in the above-identified patent and that said Letters Patent is hereby corrected as shown below:

Column 6, line 68, change "if" to --is--.

Claim 3, column 8, line 14, change "source" to --remote--.

Claim 16, column 10, line 13, change "located" to --location--.

Signed and Sealed this

Twenty-second Day of June, 1993

Attest:

MICHAEL K. KIRK

*Attesting Officer*     Acting Commissioner of Patents and Trademarks